(12) United States Patent
Molina et al.

(10) Patent No.: US 6,475,439 B1
(45) Date of Patent: Nov. 5, 2002

(54) SEALED REPLACEABLE SENSOR

(75) Inventors: Joe G. Molina, El Paso, TX (US); Jack David Rodesiler, West Chicago, IL (US)

(73) Assignee: BRK Brands, Inc., Aurora, IL (US)

( * ) Notice: Subject to any disclaimer, the term of this patent is extended or adjusted under 35 U.S.C. 154(b) by 0 days.

(21) Appl. No.: 09/481,081

(22) Filed: Jan. 11, 2000

Related U.S. Application Data

(63) Continuation of application No. 08/845,614, filed on Apr. 25, 1997, now Pat. No. 6,027,693.

(51) Int. Cl.[7] .............................................. G01N 27/00
(52) U.S. Cl. .................. 422/98; 73/31.02; 73/31.05; 204/403; 204/431; 340/628; 340/632; 422/83; 429/96
(58) Field of Search ......................... 42/98, 83; 429/96; 73/31.02, 31.05; 204/403, 431; 340/628, 632

(56) References Cited

U.S. PATENT DOCUMENTS

| | | |
|---|---|---|
| 4,238,679 A | 12/1980 | Macmillan et al. |
| 4,525,704 A | 6/1985 | Campbell |
| 4,540,980 A | 9/1985 | Porco |
| 4,608,556 A | 8/1986 | Cole |
| 5,063,164 A | 11/1991 | Goldstein |
| 5,280,273 A | 1/1994 | Goldstein |
| 5,420,440 A | 5/1995 | Ketler et al. |
| 5,661,244 A | 8/1997 | Nishinaura et al. |
| 5,694,932 A | 12/1997 | Michel |
| 5,759,846 A | * 6/1998 | Stoppini et al. |
| 5,793,295 A | 8/1998 | Goldstein |

* cited by examiner

Primary Examiner—Jan Ludlow
(74) Attorney, Agent, or Firm—Welsh & Katz, Ltd.

(57) ABSTRACT

A gas detector having a sealed sensor assembly is only exposed to the ambient atmosphere when the detector is to be placed in the service. The detector is placed in the service by removing an elongated planar adhesive backed sealing member. The gas sensor also incorporates a replaceable biomemetic sensing material which is carried within a housing within the detector. The housing contains an internal region wherein the gas sensing material is located. The internal region is sealed where the housing is attached to a printed circuit board on one hand and by the removable sealing planar member on the other hand so as to protect the gas sensitive material from contamination or exposure to the atmosphere until the unit is placed into service.

20 Claims, 3 Drawing Sheets

SEALED REPLACEABLE SENSOR

This is a continuation of Ser. No. 08/845,614, filed Apr. 25, 1997, now U.S. Pat. No. 6,027,693.

FIELD OF THE INVENTION

The invention pertains to ambient condition detectors. More particularly, the invention pertains to gas detectors alone or in combination with other types of detectors.

BACKGROUND OF THE INVENTION

Ambient condition detectors are known and are useful devices in providing a warning of a dangerous ambient condition. Representative ambient conditions include smoke, fire, heat or temperature, and gas such as carbon monoxide.

With respect to gas detectors, a variety of different types of gas sensors are known. Some of these are solid state devices, others are electrochemical devices. Another class includes biomimetic-type materials of a type disclosed in U.S. Pat. No. 5,063,164.

Materials of the above-noted type change opacity in the presence of a selected gas such as carbon monoxide. Sensors which incorporate such materials can be used to detect the presence of carbon monoxide in a region being supervised wherein the gas is present at levels and for time intervals long enough to be dangerous.

Such material perform best when installed if care is taken during manufacturer to insure that the gas sensitive materials are not exposed prematurely to either the gas or other contaminants. There thus is a need in such sensors for seals which are effective to prevent premature exposure of the material to the ambient atmosphere.

SUMMARY OF THE INVENTION

A sealed ambient condition detector incorporates a housing with an internal region. Within the housing is carried a sealed, removable gas sensing element. The gas sensing element is sealed from the ambient atmosphere until the detector is ready for use.

The gas sensing element in one aspect can be covered with a removable planar sealing member. Additionally, apertures provided on the housing for electrical connections to and from the gas sensing element can be sealed by means of a plastic, rubberized or elasto-metric sealing material in the form of a gasket.

Numerous other advantages and features of the present invention will become readily apparent from the following detailed description of the invention and the embodiments thereof, from the claims and from the accompanying drawings.

DETAILED DESCRIPTION OF THE PREFERRED EMBODIMENTS

Figure 1:
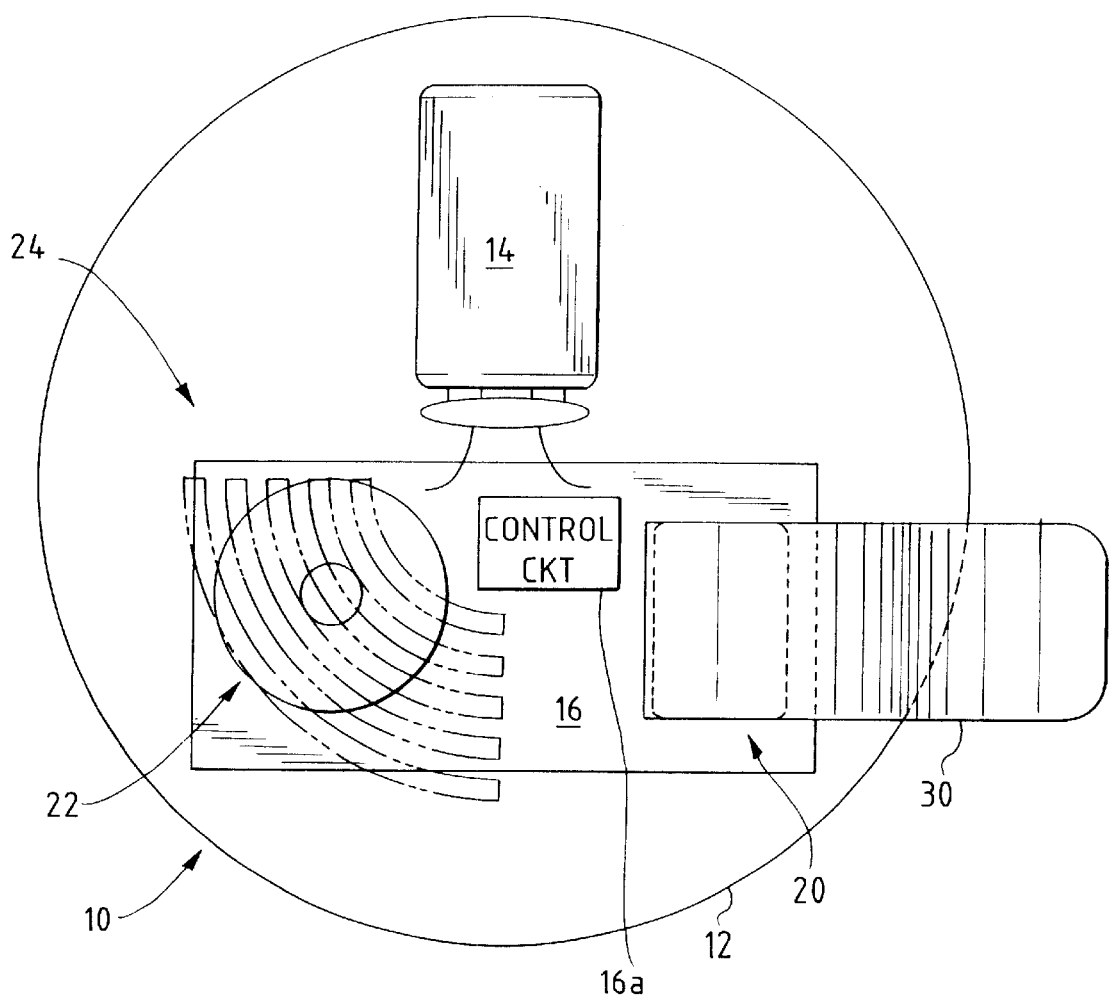
FIG. 1 is a top plan, partly schematic view of a detector incorporating a sealed gas sensor.

While this invention is susceptible of embodiment in many different forms, there are shown in the drawing and will be described herein in detail specific embodiments thereof with the understanding that the present disclosure is to be considered as an exemplification of the principles of the invention and is not intended to limit the invention to the specific embodiments illustrated.

FIG. 1 illustrates a detector 10 which could be a gas sensor, such as a carbon monoxide detector alone or a gas sensor in combination with another form of an ambient condition sensor such as smoke or temperature. The detector 10 includes a housing 12 which carries a source of electrical energy, a replaceable battery 14.

The housing 12 also carries a printed circuit board 16 to which the battery 14 is connected. The printed circuit board 16 supports a gas sensor indicated generally at 20 and a smoke sensor, which could be an ionization-type smoke sensor indicated generally at 22. Apertures 24 permit the ingress and egress of ambient atmosphere including smoke and/or gas into the housing 12. Alternately, element 22 can be a horn or other type of audible alarm device.

Figure 2:
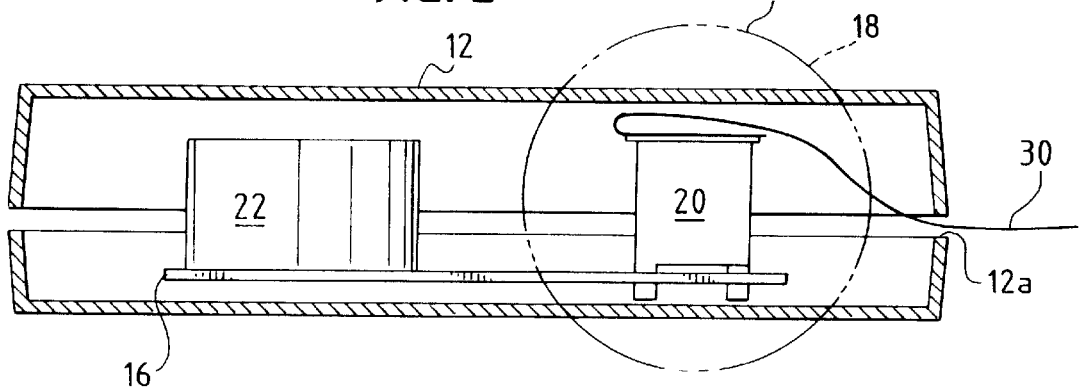
FIG. 2 is a side elevational view, partly in section, of the detector of FIG. 1.

The sensor 20 is sealed by a removable planar sealing member 30 which extends from a slot 12a in the housing 12 (best seen in FIG. 2). The member 30 is attached to the housing 12 by an adhesive layer.

When installed, the detector 10 is activated by inserting the battery 14 to energize the unit. The removable planar member 30 is pulled from the sensor 20 thereby exposing the gas sensor 20 to the adjacent ambient atmosphere.

Figure 3:
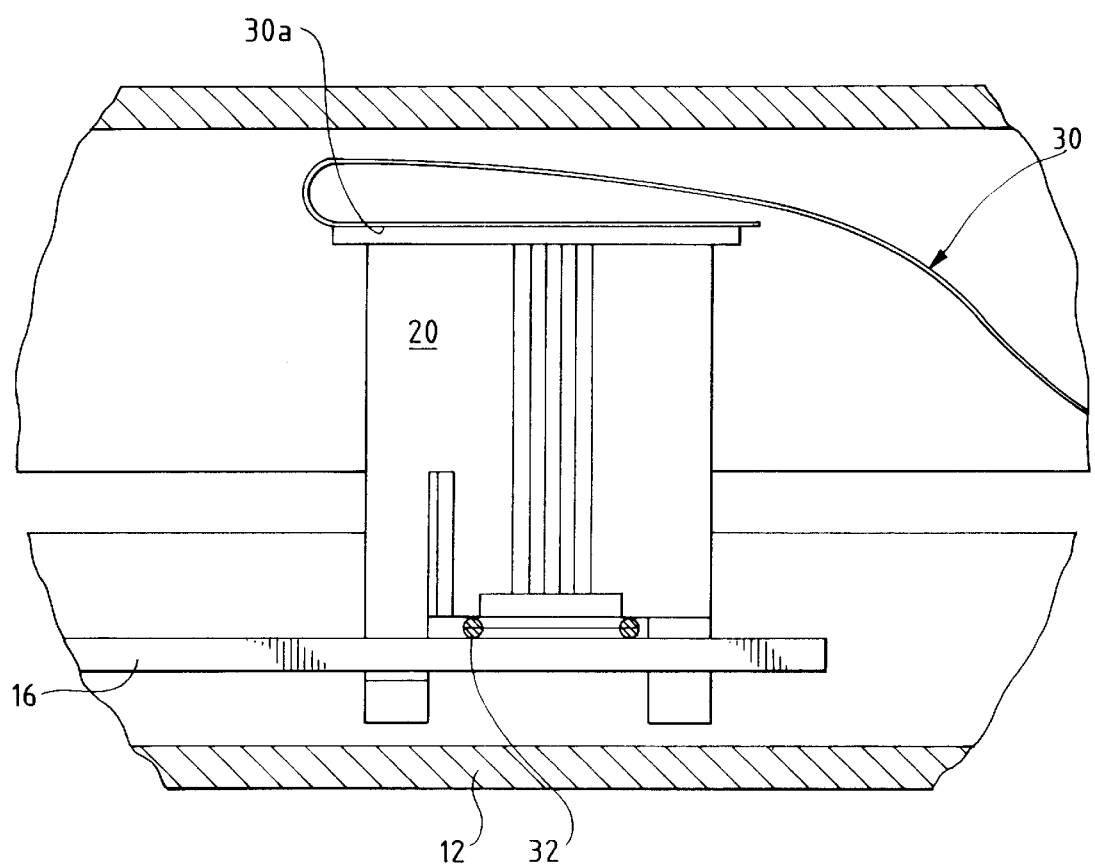
FIG. 3 is an enlarged side elevational view of a portion of FIG. 2.

FIG. 3 is an enlarged partial view of the detector 10 illustrating in more detail a region 18 indicated in FIG. 2. As is illustrated in FIG. 3, the sensor 20 is mounted on the printed circuit board 16, for example via a snap-fit.

The removable planar member 30 has an adhesive backing 30a. The member 30 can be sealed off of the sensor 20 by pulling on it. Once the member 30 has been removed, the sensor 20 will be exposed to the concentration of gas, such as carbon monoxide in the ambient atmosphere.

Figure 4:
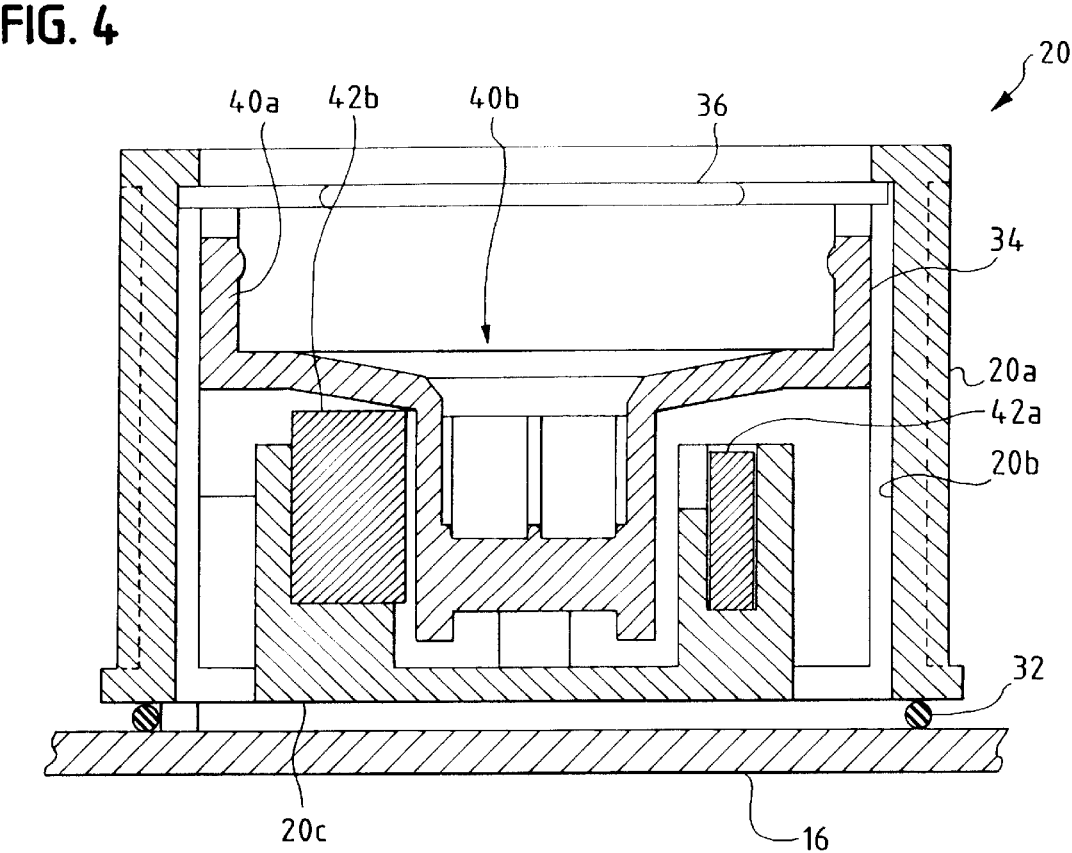
FIG. 4 is an enlarged side sectional view of the sensor of FIG. 3.

The sensor 20 is formed with a housing 20a which defines an interior volume 20b (best seen in FIG. 4). In addition to the adhesive backed flexible, removable top seal 30, the sensor 20 is also sealed, when affixed to the PC board 16 by a gasket 32. The gasket 32 can be in a variety of shapes and formed of a variety of resilient sealing materials without departing from the spirit and scope of the present invention. Gasket materials could include silicone, rubberized materials or other forms of resilient deformable sealing materials without departing from the spirit and scope of the present invention.

As is illustrated in more detail in FIG. 4, the sensor 20 carries a biomemetic sensor assembly 34 which is removably supported within the region 20b via the housing 20a.

The sensor assembly 34 is retained without the housing 20a by a wire retaining clip 36. The sensor assembly 34 includes a supporting frame 40a which carries biomemetic sensing material 40b. For replacement purposes, the frame 40a and associated sensing material 40b can be removed from the housing 20a after the retaining clip 36 has been removed. A new sensor assembly can be reinserted into the housing 20a.

The housing 20a also carries electrical components which include a source of radiant energy indicated generally at 42a and a displaced sensor of radiant energy 42b. The source 42a is energized either continuously or intermittently.

Radiant energy is projected through the material 40b to the detector 42b. As the material changes in response to ambient gas conditions, such as CO, the level of radiant energy received at the sensor 42 changes indicative of the level induration of the ambient gas. Electrical signals from the receiver or sensor 42d can be detected by control circuitry 16a mounted on the printed circuit board 16.

In response to detected signals from the sensor 42b, the control circuitry 16a can cause the detector 10 to go into alarm and admit an audible alarm.

It should be noted that as an alternate to the unit 22 functioning as a smoke detector, an audible alarm unit can be mounted at that point. In the event that the detector 10 incorporates a smoke detector and a gas detector, an audible alarm unit would be mounted elsewhere on the unit.

Figure 5:
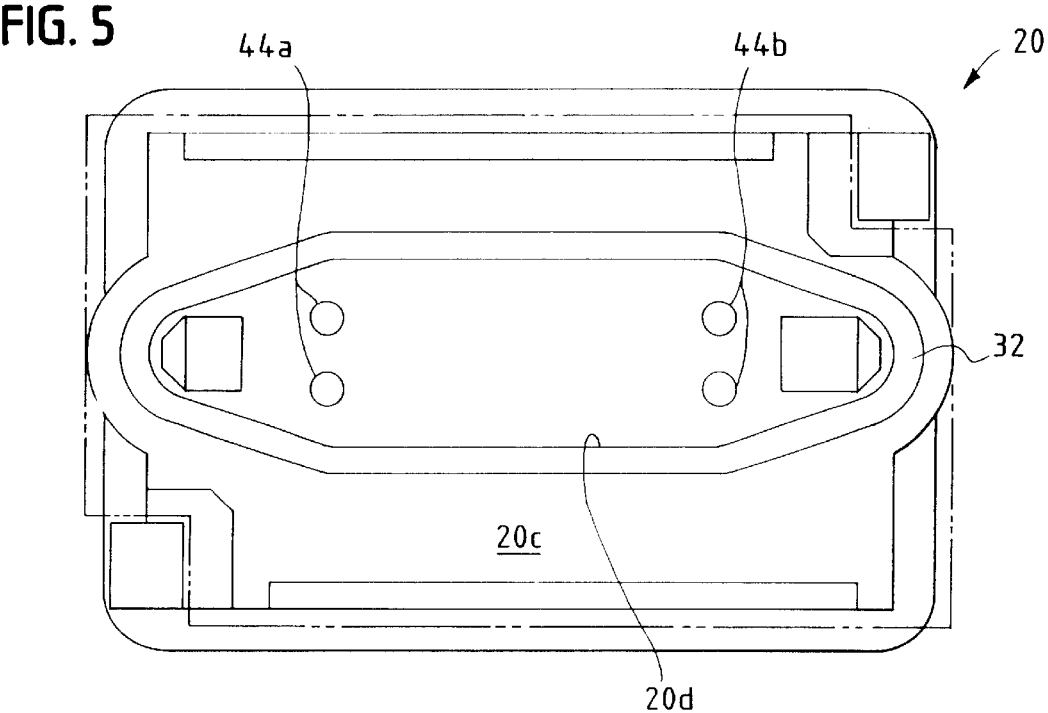
FIG. 5 is a bottom plan view of the sensor of FIG. 3.

FIG. 5 is a view of the sensor 20 looking toward surface 20c thereof which is oriented toward printed circuit board 16. The surface 20c defines an aperture 20d around which the gasket 32 forms a seal.

Electrical connections, such as the connections 44a and 44b can be made to the electrical components 42a, 42b in the region 20b within a totally sealed region of the sensor 20. Hence, the sensor 20 when assembled onto the printed circuit board with the removable sealing member 30 carried thereon represents a totally sealed sensor. Only when the detector 10 is installed and ready for use is the sensor material 40b exposed to the ambient atmosphere by removing the sealing layer 30. It would also be understood that if and when the sensor assembly 34 is replaced, another sealing layer 30a can be applied to the sensor 20 to reseal that unit. Hence, the replacement sensor assembly can be resealed until the detector is ready to be put back into service.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

What is claimed:

1. A detector comprising:
    a planar mounting member comprising a printed circuit board;
    an ambient condition sensor having an enclosure with a first opening and a second opening and first and second seals wherein said first seal surrounds said first opening and said second seal is arranged to close said second opening, and wherein said sensor comprises an electrical connection to said circuit board located within a perimeter of said first seal, wherein the sensor is attached to the printed circuit board with said first seal located adjacent to both the printed circuit board and the enclosure, and wherein the second seal is carried on the enclosure so as to preclude ambient fluids from entering the sensor
    including a housing having a region for ingress and egress of ambient atmosphere and wherein the mounting member and sensor are carried within the housing.

2. A detector as in claim 1 wherein the enclosure defines an internal region which has first and second open ends wherein one of the ends is located adjacent to the planar mounting member and is sealed from the ambient atmosphere by the first seal.

3. A detector as in claim 2 wherein the second seal removably covers the other end whereby the internal region is isolated from the ambient atmosphere at least until the second seal has been removed.

4. A detector as in claim 3 which includes a replaceable sensing element carried in the internal region.

5. A detector as in claim 4 wherein the sensing element is restrained by a removable retainer.

6. A detector as in claim 5 wherein the retainer comprises a deformable metal clip.

7. A detector as in claim 3 wherein the enclosure carries at least one mounting element for attachably engaging the planar mounting member.

8. A detector as in claim 3 which includes a control circuit carried by the mounting member and coupled to the sensor via the one end.

9. A detector as in claim 8 wherein the control circuit is located outside the enclosure.

10. A detector as in claim 8 wherein said sensor comprises a sensing circuit carried within the enclosure.

11. A detector as in claim 8 wherein an energy source is carried within the enclosure, coupled to the control circuit.

12. A detector as in claim 2 wherein the other end is displaced from the mounting member and is covered by the second seal.

13. A detector as in claim 12 wherein the one seal comprises an annular compressed seal and wherein the second seal is planar, without apertures therein and not compressed.

14. A detector as in claim 1 comprising a housing having a region for ingress and egress of ambient atmosphere and wherein said printed circuit board and said sensor are carried within the housing.

15. A detector as in claim 1 comprising electrical circuitry carried within the housing and at least in part in said sensor.

16. A detector as in claim 15 including a source of radiant energy in said sensor.

17. A detector comprising:
    a planar mounting member comprising a printed circuit board;
    an ambient condition sensor having an enclosure with a first opening and a second opening and first and second seals wherein said first seal surrounds said first opening and said second seal is arranged to close said second opening, and wherein said sensor comprises an electrical connection to said circuit board located within a perimeter of said first seal, wherein the sensor is attached to the printed circuit board with said first seal located adjacent to both the printed circuit board and the enclosure, and wherein the second seal is carried on the enclosure so as to preclude ambient fluids from entering the sensor;

a housing having a region for ingress and egress of ambient atmosphere and wherein said printed circuit board and said sensor are carried within the housing;

wherein a portion of the second seal extends outside the housing to facilitate removal of said second seal.

18. A detector as in claim 17 wherein said second seal comprises an elongated, planar flexible member.

19. A detector comprising:

a planar mounting member;

a sealed ambient condition sensor having first and second seals wherein the sensor is attached to the mounting member with one seal located adjacent to both the mounting member and the sensor, and wherein the second seal is carried on the sensor so as to preclude ambient fluids from entering the sensor; a housing having a region for ingress and egress of ambient atmosphere and wherein the mounting member and sensor are carried within the housing; and wherein a portion of the second seal extends from the housing to facilitate removal of same.

20. A detector as in claim 19 wherein the second seal comprises an elongated, planar flexible member.

* * * * *